(12) United States Patent
Fukunishi et al.

(10) Patent No.: US 7,105,694 B2
(45) Date of Patent: Sep. 12, 2006

(54) O-ISOPROPYL ISOUREA SALT AND PRODUCTION METHOD THEREOF

(75) Inventors: Youichi Fukunishi, Uozu (JP); Shinichi Kakinuma, Uozu (JP); Kenichi Ishii, Uozu (JP); Masahiro Murotani, Toyama (JP)

(73) Assignee: Nippon Carbide Kogyo Kabushiki Kaisha, Tokyo (JP)

( * ) Notice: Subject to any disclaimer, the term of this patent is extended or adjusted under 35 U.S.C. 154(b) by 176 days.

(21) Appl. No.: 10/509,626

(22) PCT Filed: Jan. 21, 2004

(86) PCT No.: PCT/JP2004/000484

§ 371 (c)(1),
(2), (4) Date: Sep. 29, 2004

(87) PCT Pub. No.: WO2004/067500

PCT Pub. Date: Aug. 12, 2004

(65) Prior Publication Data

US 2005/0171372 A1    Aug. 4, 2005

(30) Foreign Application Priority Data

Jan. 29, 2003    (JP)    ............... 2003-019621

(51) Int. Cl.
*C07C 273/00*    (2006.01)
*C07C 275/00*    (2006.01)

(52) U.S. Cl. .......................................... 558/8
(58) Field of Classification Search .................. 558/8
See application file for complete search history.

(56) References Cited

U.S. PATENT DOCUMENTS 3,551,489 A    12/1970  Schaefer et al.
3,931,316 A    1/1976   Weiss

FOREIGN PATENT DOCUMENTS

| DE | 2358904 A1    | 6/1975  |
| DE | 27 08 973 A1  | 9/1978  |
| GB | 1194313 B1    | 6/1970  |
| GB | 1294442 B1    | 10/1972 |
| JP | 52-024007 A1  | 6/1977  |
| JP | 62-022751 A1  | 1/1987  |
| JP | 04-089467 A2  | 3/1992  |
| JP | 09-012530 A1  | 1/1997  |
| JP | 10-029983 A1  | 2/1998  |

OTHER PUBLICATIONS

EPO Search Report mailed on Sep. 20, 2005.
International Search Report for PCT/JP2004/000484 mailed on Apr. 27, 2004.

*Primary Examiner*—Peter O'Sullivan
(74) *Attorney, Agent, or Firm*—Rader, Fishman & Grauer PLLC

(57) ABSTRACT

O-isopropyl-isourea hydrogen sulfate or sulfate represented by the formula (I):

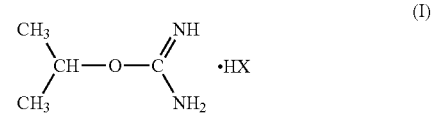

wherein X represents $HSO_4$ or ½ $SO_4$ and the production method thereof, wherein O-isopropyl-isourea hydrogen sulfate is obtained by reacting cyanamide and isopropyl alcohol in the presence of sulfuric acid and is neutralized with an alkali metal hydroxide to produce O-isopropyl-isourea sulfate.

8 Claims, No Drawings

O-ISOPROPYL ISOUREA SALT AND PRODUCTION METHOD THEREOF

TECHNICAL FIELD

The present invention relates to an O-isopropyl-isourea hydrogen sulfate or sulfate, which is a novel compound useful as important intermediates for pharmaceuticals, agricultural chemicals, and industrial chemicals, and a production method thereof.

BACKGROUND ART

In the part, O-isopropyl-isourea hydrochloride is known in the art and the physical properties thereof are disclosed in, for example, JP-A-9-12530. In addition, regarding the O-methyl-isourea sulfate and hydrogen sulfate, the physical properties thereof are disclosed in, for example, U.S. Pat. No. 3,931,316 and JP-B-52-24007.

However, 1) O-isopropyl-isourea sulfate and 2) O-isopropyl-isourea hydrogen sulfate both according to the present invention are not described in the above patent publications and chemical Abstract and, since these compounds are not described in other publications as long as the present inventors know, these compounds are believed to be novel.

Further, many production methods regarding the production of salts of O-alkyl-isourea are proposed. For example, salts, such as hydrochloride, hydrogen sulfate, sulfate, acetate, organic sulfonate, etc., of O-methyl-isourea are obtained from, for example, methanol, cyanamide and various acids.

Similarly, regarding O-ethyl-isourea, the hydrochloride, hydrogen sulfate and organic sulfonates are obtained.

However, regarding O-isopropyl-isourea, only the hydrochloride and organic sulfonates are reported, but the production methods thereof are not satisfied as the industrial methods.

U.S. Pat. No. 3,931,316 and British Patent No. 1194313 disclose that, when a concentrated hydrogen chloride is added to an isopropyl alcohol solution of cyanamide to thereby be reacted, O-isopropyl-isourea hydrochloride is reported to be obtained. However, the yield thereof is as extremely low as 38% and, therefore, this method is not suitable as an industrial process.

Furthermore, JP-A-9-12530 discloses a production method of O-isopropyl-isourea hydrochloride using chloroform amidinium chloride. According to this method, a high purity crystalline O-isopropyl-isourea hydrochloride is obtained at a yield of 82% by the reaction of chloroform amidinium chloride, cyanamide and isopropyl alcohol.

However, since chloroform amidinium chloride is very expensive and since the yield of the production thereof from cyanamide is low, the above-production is not suitable as an industrial process.

Furthermore, JP-A-10-29983 discloses that O-isopropyl-isourea hydrochloride is obtained by reacting cyanamide and isopropyl alcohol in the presence of hydrogen chloride.

However, the use of hydrogen chloride requires the use of the special equipments and produces isopropyl chloride as a by-product. This substance has mutation inducing characteristics and has a high volatility. Accordingly, this production method has a possibility to impart an adverse affect to environment and therefore is not industrially preferable.

Furthermore, in JP-A-62-22751, it is disclosed that O-isopropyl-isourea dodecylbenzene sulfonate is obtained from isopropyl alcohol, cyanamide and dodecylbenzene sulfonic acid at a yield of 97.6%.

However, dodecylbenzene sulfonic acid is also very expensive, this method is not industrially preferable.

DISCLOSURE OF INVENTION

The present inventors studied the production of the above-mentioned novel compound, O-isopropyl-isourea hydrogen sulfate or sulfate from a less expensive starting material in an environmentally acceptable method, in order to obtain the desired compound.

The above-mentioned problem have been solved by reacting cyanamide and isopropyl alcohol in the presence of sulfuric acid to thereby obtain O-isopropyl-isourea hydrogen sulfate at a high yield. The sulfate can be obtained by neutralizing the above hydrogen sulfate with an alkali metal hydroxide:

O-isopropyl-isourea hydrogen sulfate or sulfate Represented by the Formula (I):

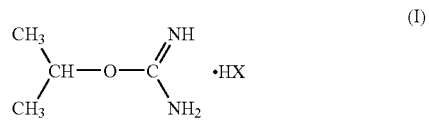

wherein X represents $HSO_4$ or $\frac{1}{2}$ $SO_4$.

BEST MODE FOR CARRYING OUT THE INVENTION

The mode of carrying out the present invention will now be explained in detail.

The cyanamide used as a main starting material of O-isopropyl-isourea hydrogen sulfate preferably has a lower water content from the viewpoint of a yield. Typically, the water content is preferably 2% by weight or less. This is because the higher water content leads to the increase in the concentration of urea formed by a side reaction. Therefore, the use of crystalline cyanamide, as a starting cyanamide, is preferable.

As the sulfuric acid, the use of concentrated sulfuric acid having a concentration of 95% or more is preferable due to the same reason mentioned above. The amount of the sulfuric acid used is preferably 0.9–1.2 mol, more preferably 1.0 mol, based upon 1 mol of the cyanamide.

The amount of the isopropyl alcohol used is preferably 2–10 mol, more preferably 3–8 mol, based upon 1 mol of the cyanamide, from the viewpoints of preventing the occurrence of the urea formation reaction.

The reaction temperature is preferably 30° C. or less, more preferably 5–20° C. and the reaction time is approximately 2–24 hours.

The above-mentioned reaction product is in the form of an isopropyl alcohol solution of O-isopropyl-isourea hydrogen sulfate. The resultant O-isopropyl-isourea hydrogen sulfate can be used, without isolating, for the reaction of, for example, guanidination reaction and pyrimidination reaction in the form of the solution, but the sulfate salt form can be isolated as follows.

After an alkaline compound is added to the above-mentioned O-isopropyl-isourea hydrogen sulfate, the resultant sulfate of the alkaline compound is removed by, for example, a conventional method such as filtration to obtain a solution of O-isopropyl-isourea sulfate. The resultant solution is concentrated under vacuo and the crystalline was precipitated by the addition of a poor solvent such as acetone and the precipitated crystal was removed by, for example, filtration, followed by drying, whereby O-isopropyl-isourea sulfate can be obtained.

Examples of the above alkaline compound are, for example, hydroxides of alkali metals, hydroxides of alkaline earth metals. Among these alkaline compounds, the use of sodium hydroxide, potassium hydroxide is especially preferable from the viewpoints of good reactivity and easy operation of the separation of the crystalline. As the form of the alkaline compounds, about 40%, for example, of the aqueous solution is preferable from the viewpoints of, for example, the good reactivity and the quality of the O-isopropyl-isourea sulfate.

The amounts of the alkaline compound used are varied by, for example, the yield of the O-isopropyl-isourea hydrogen sulfate, etc. Practically, the concentration of acids in the reaction mixture was determined by a potentiometric titration and the amount of the alkaline compounds preferably used is calculated by the first infection point of the result of the potentiometric titration.

According to the present method, O-isopropyl-isourea sulfate having a purity of at least 97% or more can be obtained when the amount of the alkaline compound to be used is decided by the analysis of potentiometric titration.

Furthermore, when 1 mole of the resultant O-isopropyl-isourea sulfate and ½ mole of sulfuric acid are reacted to form O-isopropyl-isourea hydrogen sulfate. The resultant O-isopropyl-isourea can be isolated by concentrating to dryness or by dispersing in a poor solvent.

EXAMPLES

The present invention will now be further explained in detail with reference to the following Examples, but is by no means limited to these Examples.

Example 1

To a 300 ml four-necked flask provided with a stirrer, a thermometer and a starting material charge device, 120.40g (2.0 mol of isopropyl alcohol) and 21.24 g (purity 99%, 0.5 mol) of crystalline cyanamide were charged, followed by agitating to be dissolved. After dissolving, 50.56 g (conc. 97%, 0.5 mol) of conc. sulfuric acid was dropwise added over about 1.5 hour in such a manner that the temperature of the reaction solution does not exceed 25° C.

After the completion of the dropwise addition, the reaction solution was further aged at 25° C. or less for 20 hours, to thereby obtain an isopropyl alcohol solution of O-isopropyl-isourea hydrogen sulfate. The yield according to the analysis with a potentiometric titration was 89.2% (based upon the cyanamide).

Example 2

While the reaction solution obtain in Example 1 above was agitated and cooled, 46.40 g (0.46 mol) of 40% aqueous sodium hydroxide solution was added thereto. After the white crystal thus formed was removed by filtration under vacuum, the crystal was washed with 34.4 g of isopropyl alcohol. The filtrate and the wash solution were combined, followed by concentrating under vacuo to thereby obtain 83.35 g of a high density liquid. To the resultant high viscosity solution, 246.3 g of acetone was added to thereby form white crystals of O-isopropyl-isourea sulfate. The resultant crystal was separated by a filtration under vacuum, followed by vacuum drying at room temperature to thereby obtain 45.30 g of the O-isopropyl-isourea.

The purity analyzed by a potentiometric titration was 97.2% and the yield was 58.3%, based upon cyanamide.

Example 3

To a 500 ml four-necked flask provided with a stirrer, a thermometer and a starting material charge device, 64.29 g of distilled water and 64.29 g of conc. sulfuric acid (concentration 98.1%, 0.64 mol) were charged, while cooling, and 200 g of O-isopropyl-isourea sulfate (purity 97.2%, 1.29 mol) was added thereto, while stirring. The reaction solution was concentrated under vacuo and the concentrated mixture was dispersed in hexane, followed by separating the precipitated crystal by filtration under vacuo. Thus, 244.49 of O-isopropyl-isourea hydrogen sulfate was obtained by drying at room temperature under vacuo.

The purity analyzed by potentiometric titration was 96.6% and the yield was 91.7%, based upon O-isopropyl-isourea sulfate.

The analysis results of each substance is as follows.

1) O-isopropyl-isourea

1H-NMR(CDC13, TMS, 200 MHz) δ (ppm); 1.38(d, J=6.03 Hz, 6H, CH3—CH(CH3)—O—), 4.93(m, 1H, CH3—CH(CH3)—O—), 4.93(s, 4H, —C—NH2(=NH2))
13C-NMR(CDC13, TMS, 50 MHz) δ (ppm); 22.7(CH3—CH(CH3)—O—), 77.5(CH3—CH(CH3)—O—), 163.8(—O—C—NH2(=NH2))

IR Analysis

| Characteristic absorption band/cm$^{-1}$ | Identification | Intensity*[1] |
|---|---|---|
| 3293 | N—H (symmetric stretch) | vs |
| 1682 | N—H (deformation) | vs |
| 1543 | C=N (stretch) | m |
| 1465 | C—H (deformation) | w |
| 1389 | C—H (deformation, zeminal) | w |
| 1188 | S=O (antisymmetric stretch) | w |
| 1143 | C—O—C (antisymmetric stretch) | s |
|  | finger-print region | w |

*[1]vs: Very strong
s: Strong
m: Medium
w: Weak
Melting point: 152.6° C.

2) O-isopropyl-isourea hydrogen sulfate

1H-NMR (CDC13, TMS, 200 MHz) δ (ppm); 1.41 (d, J=6.03 Hz, 6H, CH3—CH(CH3)—O—), 4.95 (m, 1H, CH3—CH(CH3)—O—), 4.98 (s, 4H, —C—NH2(=NH2))
13C-NMR (CDC13, TMS, 50 MHz) δ (ppm); 22.7 (CH3—CH(CH3)—O—), 78.2 (CH3—CH(CH3)—O—), 163.8 (—O—C—NH2(=NH2))

IR Analysis

| Characteristic absorption band/cm$^{-1}$ | Identification | Intensity*[1] |
|---|---|---|
| 3117 | N—H (symmetric stretch) | vs |
| 1678 | N—H (deformation) | vs |
| 1557 | C=N (stretch) | m |
| 1465 | C—H (deformation) | w |
| 1385 | C—H (deformation, zeminal) | w |

-continued

| Characteristic absorption band/cm$^{-1}$ | Identification | Intensity*[1] |
|---|---|---|
| 1188 | S=O (antisymmetric stretch) | w |
| | finger-print region | w |

*[1]As mentioned above
Melting point: 87.3° C.

INDUSTRIAL APPLICABILITY

O-isopropyl-isourea hydrogen sulfate or sulfate, which is useful as important intermediates for pharmaceuticals, agricultural chemicals and industrial chemicals, can be obtained at a good yield with an industrial production method without generating environmental problems.

The invention claimed is:

1. O-isopropyl-isourea hydrogen sulfate or sulfate represented by the formula (I):

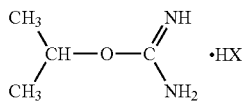
(I)

wherein X represents HSO$_4$ or ½ SO$_4$.

2. A method for producing O-isopropyl-isourea hydrogen sulfate comprising reacting cyanamide and isopropyl alcohol in the presence of sulfuric acid.

3. A method for producing O-isopropyl-isourea sulfate by neutralizing the O-isopropyl-isourea hydrogen sulfate which is obtained by the method according to claim 2, with an alkali metal hydroxide.

4. A method for producing O-isopropyl-isourea hydrogen sulfate as claimed in claim 2 or 3, wherein a mole ratio of the sulfuric acid to the cyanamide is 0.9–1.2 mol based upon 1 mol of the cyanamide.

5. A method for producing O-isopropyl-isourea hydrogen sulfate as claimed in claim 2 or 3, wherein the sulfuric acid is concentrated sulfuric acid.

6. A method for producing O-isopropyl-isourea hydrogen sulfate as claimed in claim 5, wherein the concentration of the concentrated sulfuric acid is 95% by weight or more.

7. A method for producing O-isopropyl-isourea hydrogen sulfate as claimed in claim 2 or 3, wherein a mol ratio of cyanamide and isopropyl alcohol is 1:2 to 10.

8. A method for producing O-isopropyl-isourea hydrogen, sulfate as claimed in claim 2 or 3, wherein the reaction temperature is 0° C.–30° C.

* * * * *